US012558571B2

(12) United States Patent
Kang et al.

(10) Patent No.: US 12,558,571 B2
(45) Date of Patent: Feb. 24, 2026

(54) ULTRASONIC IRRADIATION DEVICE, IRRADIATION METHOD THEREOF

(71) Applicant: GODIUS CO., LTD., Seoul (KR)

(72) Inventors: Dong Hwan Kang, Seoul (KR); Sun Kim, Seoul (KR); Hyun Sook Lee, Seoul (KR); Jung Su Jeon, Seoul (KR)

(73) Assignee: Godius Co., Ltd., Seoul (KR)

( * ) Notice: Subject to any disclaimer, the term of this patent is extended or adjusted under 35 U.S.C. 154(b) by 0 days.

(21) Appl. No.: 18/929,862

(22) Filed: Oct. 29, 2024

(65) Prior Publication Data

US 2025/0375626 A1    Dec. 11, 2025

(30) Foreign Application Priority Data

Jun. 5, 2024    (KR) ........................ 10-2024-0073387

(51) Int. Cl.
    *A61N 7/00*      (2006.01)
    *A61B 17/22*      (2006.01)
    *A61B 17/00*      (2006.01)

(52) U.S. Cl.
    CPC ................ *A61N 7/00* (2013.01); *A61B 17/22* (2013.01); *A61B 2017/00106* (2013.01); *A61B 2017/00123* (2013.01); *A61B 2017/00132* (2013.01); *A61B 2017/22008* (2013.01); *A61B 2017/22028* (2013.01); *A61N 2007/0095* (2013.01)

(58) Field of Classification Search
    CPC ...................................................... A61N 7/02
    See application file for complete search history.

(56) References Cited

U.S. PATENT DOCUMENTS

| | | | | |
|---|---|---|---|---|
| 6,413,216 B1* | 7/2002 | Cain | ................. | A61M 37/0092 |
| | | | | 424/9.5 |
| 11,524,183 B1* | 12/2022 | Garcia Gutierrez | ... | A61B 34/25 |
| 2001/0014819 A1* | 8/2001 | Ingle | ................. | A61B 18/1482 |
| | | | | 128/898 |
| 2003/0018255 A1* | 1/2003 | Martin | ............... | A61B 17/2251 |
| | | | | 600/437 |
| 2003/0060736 A1* | 3/2003 | Martin | ..................... | A61N 7/02 |
| | | | | 601/2 |
| 2003/0187371 A1* | 10/2003 | Vortman | .................. | A61N 7/02 |
| | | | | 601/3 |
| 2004/0039312 A1* | 2/2004 | Hillstead | .............. | A61B 8/4494 |
| | | | | 601/2 |
| 2015/0005756 A1* | 1/2015 | Tillander | ........... | G01R 33/4804 |
| | | | | 606/27 |
| 2016/0144203 A1* | 5/2016 | Holland | ................... | A61N 7/00 |
| | | | | 601/2 |
| 2021/0212709 A1* | 7/2021 | Pernot | ................. | A61B 8/5269 |

FOREIGN PATENT DOCUMENTS

JP          6861624 B2     4/2021

\* cited by examiner

*Primary Examiner* — Colin T. Sakamoto

(74) *Attorney, Agent, or Firm* — Leydig, Voit & Mayer Ltd.

(57) ABSTRACT

An ultrasonic irradiation device includes: an ultrasonic irradiator configured to irradiate ultrasound; a detector configured to acquire cavitation information from the body; and a processor configured to control the ultrasonic irradiator, based on the acquired cavitation information, to irradiate ultrasound to a focal point for an irradiation area of a body or to not irradiate ultrasound.

20 Claims, 4 Drawing Sheets

(a) First focus point for each irradiation area (b) Second focus point for each irradiation area (c) Third focus point for each irradiation area (a) First focus point for each irradiation area (b) Second focus point for each irradiation area (c) Third focus point for each irradiation area

ULTRASONIC IRRADIATION DEVICE, IRRADIATION METHOD THEREOF

CROSS-REFERENCE TO RELATED APPLICATIONS

This application claims benefit to Korean Patent Application No. KR10-2024-0073387, filed on Jun. 5, 2024, which is incorporated by reference herein in its entirety.

FIELD

The present disclosure relates to an ultrasonic irradiation device and an irradiation method thereof.

BACKGROUND

Ultrasound imaging devices utilizes the penetration and reflection properties of ultrasound. For example, there is a device that visualizes the time and intensity of reflection as ultrasound penetrates the human body and penetrates each organ, thereby obtaining a cross-sectional image of the human body.

In addition, there is an ultrasound irradiation device that burns and removes specific subcutaneous tissues, such as tumors in the skin, or induces degeneration and regeneration of skin tissue by utilizing the heat generated by high intensity focused ultrasound (HIFU).

However, conventional ultrasound image processing devices are not capable of identifying the location where the ultrasound is focused and the process of tumor degeneration during ultrasound irradiation.

In addition, since conventional ultrasonic irradiation devices require a doctor to carefully conduct ultrasonic irradiation, there are limitations in shortening the irradiation time and in maximizing the ultrasonic irradiation effect.

SUMMARY

In an exemplary embodiment, the present disclosure provides an ultrasonic irradiation device. The ultrasonic irradiation device includes: an ultrasonic irradiator configured to irradiate ultrasound; a detector configured to acquire cavitation information from the body; and a processor configured to control the ultrasonic irradiator, based on the acquired cavitation information, to irradiate ultrasound to a focal point for an irradiation area of a body or to not irradiate ultrasound.

In another exemplary embodiment, the present disclosure provides an ultrasonic irradiation method. The method includes: irradiating, by an ultrasonic irradiator of an ultrasonic irradiation device, ultrasound to a body; acquiring, by a detector of the ultrasonic irradiation device, cavitation information in the body; and controlling, by a processor of the ultrasonic irradiation device, based on the cavitation information, the ultrasonic irradiator to irradiate ultrasound to a focal point for an irradiation area of the body or to not irradiate ultrasound.

In yet another exemplary embodiment, the present disclosure provides a non-transitory computer-readable medium having processor-executable instructions stored thereon. The processor-executable instructions, when executed, facilitate performance of the following: irradiating, by an ultrasonic irradiator of an ultrasonic irradiation device, ultrasound to a body; acquiring, by a detector of the ultrasonic irradiation device, cavitation information in the body; and controlling, by a processor of the ultrasonic irradiation device, based on the cavitation information, the ultrasonic irradiator to irradiate ultrasound to a focal point for an irradiation area of the body or to not irradiate ultrasound.

BRIEF DESCRIPTION OF THE FIGURES

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figures 1, 2:
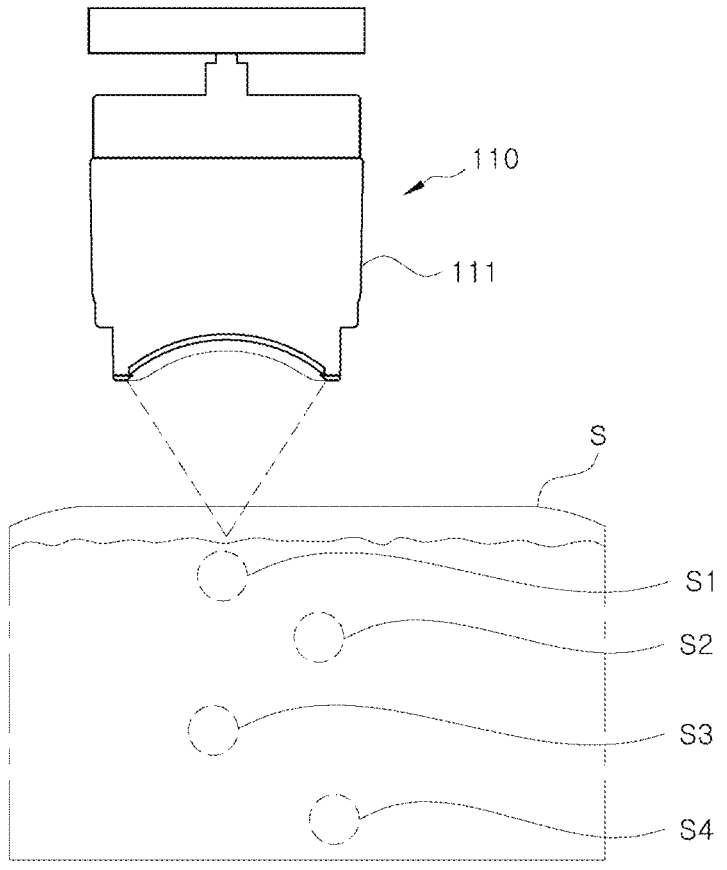
FIG. 1 is a diagram illustrating an example of an ultrasonic irradiation device according to the present disclosure.
FIG. 2 is a diagram illustrating an example of a process for operating the ultrasonic irradiation device shown in FIG. 1.

Exemplary embodiments of the present disclosure provide an ultrasonic irradiation device and an irradiation method thereof, which can accurately irradiate ultrasound to a specific part of a body without damaging normal tissues in the body, thereby improving the accuracy of ultrasonic irradiation.

Exemplary embodiments of the present disclosure further provide an ultrasonic irradiation device and an irradiation method thereof, which can control and irradiate ultrasound to respective parts of a body using optimal condition(s) for each respective part of the body, thereby reducing an irradiation time while maximizing the ultrasonic irradiation effect.

It will be appreciated that technical problems addressed by the present disclosure are not limited to the technical problems mentioned above.

In an aspect of the present disclosure, an ultrasonic irradiation device may include an ultrasonic irradiator configured to irradiate ultrasound to a body; an acquisition module (e.g., a detector) configured to acquire cavitation information from the body; and a processor configured to: based on the cavitation information, control the ultrasonic irradiator to apply preset ultrasonic energy linked to a focus point for each irradiation area of the body, or to not apply the ultrasonic energy.

Furthermore, the ultrasonic irradiator may irradiate the ultrasound based on an electronic beam steering scheme.

Furthermore, the acquisition module may include a passive cavitation detector (PCD) to acquire the cavitation information.

Furthermore, the processor may be configured to determine whether a tumor is being treated based on the cavitation information.

Furthermore, the processor may be configured to, based on cavitation information acquired by the irradiation of the ultrasonic energy not meeting a preset condition, control the ultrasonic irradiator to adjust the ultrasonic energy or stop the irradiation.

Furthermore, the processor may be configured to, based on cavitation information being acquired which indicates cavitation in an area other than the area set to be irradiated with the ultrasound, control the ultrasonic irradiator to adjust the ultrasonic energy or stop the irradiation.

Furthermore, the processor may be configured to determine at least one of an acquisition position or an acquisition angle of the acquisition module to acquire the cavitation information according to a transmission signal position of the ultrasonic irradiator.

Furthermore, the processor may be configured to, based on a transmission path of the ultrasonic irradiator being changed, control at least one of an acquisition position or an acquisition angle of the acquisition module to acquire the cavitation information based on a cavitation channel corresponding to the changed transmission path.

Furthermore, the processor may be configured to control the ultrasonic irradiator to apply the ultrasonic energy with a preset time delay at each transmission signal position of the ultrasonic irradiator.

Furthermore, the processor may be configured to control the ultrasonic irradiator to apply the ultrasonic energy based on at least one of a preset irradiation time or intensity linked to a transmission signal position of the ultrasonic irradiator and the focus point for each irradiation area.

Furthermore, in another aspect of the present disclosure, an ultrasonic irradiation method performed by an ultrasonic irradiation device may include irradiating, by an ultrasonic irradiator of the ultrasonic irradiation device, ultrasound to a body; acquiring, by an acquisition module of the ultrasonic irradiation device, cavitation information from the body; and controlling, by a processor of the ultrasonic irradiation device, based on the cavitation information, to apply preset ultrasonic energy linked to a focus point for each irradiation area of the body, or to not apply the ultrasonic energy.

In addition, a computer program stored in a non-transitory computer-readable recording medium may be further provided to perform a method for monitoring ultrasound image by being combined with a computer as hardware.

In addition, a non-transitory computer-readable recording medium recording a computer program for executing a method for implementing the present disclosure may be further provided.

In the drawings, the same reference numeral refers to the same element. This disclosure does not necessarily describe all elements of embodiments, and general contents in the technical field to which the present disclosure belongs or repeated contents of the embodiments may be omitted. The terms, such as "unit, module, member, and block" may be embodied as hardware or software, and a plurality of "units, modules, members, and blocks" may be implemented as one element, or a unit, a module, a member, or a block may include a plurality of elements.

Throughout this specification, when a part is referred to as being "connected" to another part, this includes "direct connection" and "indirect connection", and the indirect connection may include connection via a wireless communication network. Furthermore, when a certain part "includes" a certain element, other elements are not excluded unless explicitly described otherwise, and other elements may in fact be included.

Furthermore, when a certain part "includes" a certain element, other elements are not excluded unless explicitly described otherwise, and other elements may in fact be included.

In the entire specification of the present disclosure, when any member is located "on" another member, this includes a case in which still another member is present between both members as well as a case in which one member is in contact with another member.

The terms "first," "second," and the like are just to distinguish an element from any other element, and elements are not limited by the terms.

The singular form of the elements may be understood into the plural form unless otherwise specifically stated in the context.

Identification codes in each operation are used not for describing the order of the operations but for convenience of description, and the operations may be implemented differently from the order described unless there is a specific order explicitly described in the context.

Hereinafter, operation principles and embodiments of the present disclosure will be described with reference to the accompanying drawings.

A controller of an ultrasonic irradiation device according to the present disclosure includes various devices that may perform computational processing and provide results to a user. For example, the controller of the ultrasonic irradiation device may include a computer, a server device, and a portable terminal, or may be in the form of one of them.

Here, the computer may include, for example, a notebook, a desktop, a laptop, a tablet PC, a slate PC, and the like mounted with a web browser.

The server device is a server that communicates with an external device to process information, and may include an application server, a computing server, a database server, a file server, a mail server, a proxy server, and a web server.

A portable terminal is a wireless communication device that ensures portability and mobility, and may include all kinds of handheld-based wireless communication devices such as PCS (Personal Communication System), GSM (Global System for Mobile communications), PDC (Personal Digital Cellular), PHS (Personal Handyphone System), PDA (Personal Digital Assistant), IMT (International Mobile Telecommunication)-2000, CDMA (Code Division Multiple Access)-2000, W-CDMA (W-Code Division Multiple Access), WiBro (Wireless Broadband Internet) terminal, a smart phone, and the like, and a wearable device such as at least one of a watch, a ring, bracelets, anklets, a necklace, glasses, contact lenses, or a head-mounted device (HMD).

The ultrasonic irradiation device according to the present disclosure may control the ultrasonic irradiator to apply preset ultrasonic energy linked to a focus point for each irradiation area of the body, or to not apply the ultrasonic energy based on the cavitation information.

The ultrasonic irradiation device according to the present disclosure can accurately irradiate ultrasound to a specific part of a body without damaging normal tissues in the body, thereby improving the accuracy of ultrasonic irradiation. In addition, the ultrasonic irradiation device according to the present disclosure may control and irradiate ultrasound to respective parts of a body using optimal condition(s) for each respective part of the body, thereby reducing an irradiation time while maximizing the ultrasonic irradiation effect.

Hereinafter, an exemplary embodiment of the ultrasonic irradiation device will be described in detail.

FIG. 1 is a diagram illustrating a configuration of an ultrasonic irradiation device according to the present disclosure. FIG. 2 is a diagram illustrating an example of a process in which the ultrasonic irradiator shown in FIG. 1 irradiates ultrasound.

Figure 3:
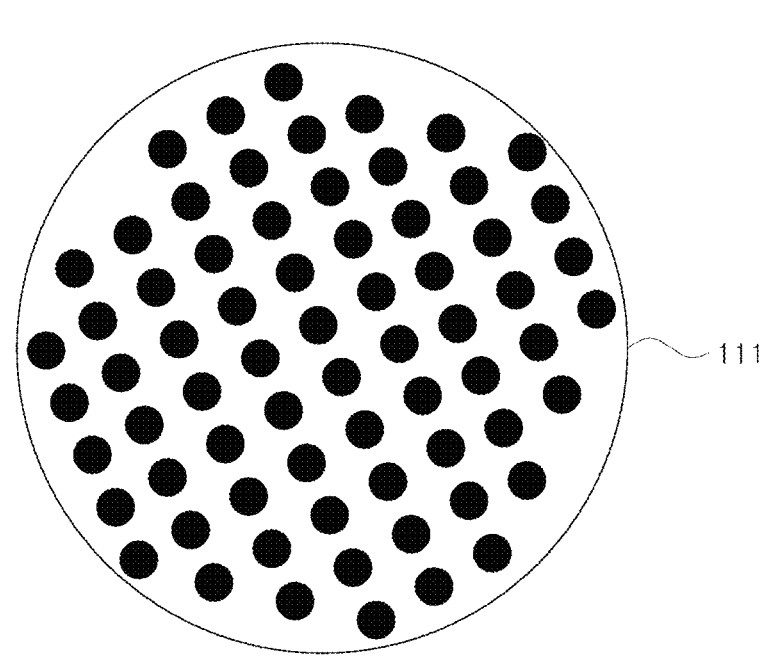
FIG. 3 is a diagram illustrating an example of a transducer of the ultrasonic irradiation device shown in FIG. 2.

FIG. 3 is a diagram illustrating an example of a transducer of the ultrasonic irradiator shown in FIG. 2.

Referring to FIGS. 1 to 3, an ultrasonic irradiation device 100 may include an ultrasonic irradiator 110, an acquisition module 120, and a controller 130.

The ultrasonic irradiator 110 may irradiate ultrasonic waves to a human body S according to the ultrasonic focusing depth. Here, the ultrasonic irradiator 110 may include a plurality of transducer arrays 111. For example, the human body S may include one or more organs. The one or more organs may include at least one of an organ S1 of the respiratory organs, an organ S2 of the digestive organs, an organ S3 of the reproductive organs, or an organ S4 of the urinary organs.

Here, the ultrasonic irradiator 110 may irradiate ultrasound based on an electronic beam steering scheme. The electronic beam steering may be a method of applying ultrasound energy to a focus point with a preset time delay when the position of the target focus point is changed.

The acquisition module 120 is provided in the transducer array 111 and may acquire cavitation information from the human body S while the ultrasound is irradiated. The acquisition module 120 may include a passive cavitation detector (PCD) to acquire cavitation information while monitoring the cavitation. For example, the acquisition module 120 may acquire cavitation information corresponding to cavitation occurring in at least one of the respiratory organs S1, the digestive organs S2, the reproductive organs S3, or the urinary organs S4. Here, cavitation refers to a phenomenon in which a cavity is formed in a fluid due to a pressure change caused by a change in the velocity of the fluid. In this case, the cavity phenomenon refers to a phenomenon in which vapor bubbles are generated in the liquid because the pressure of the liquid is lowered below the vapor pressure when the liquid moves at a high velocity.

Since the acquisition position of the acquisition module 120 for acquiring the cavitation information also changes according to the transmission signal position of the ultrasonic irradiator 110 according to the present disclosure, the sensing signal for cavitation may be acquired efficiently. In addition, according to the present disclosure, the position where ultrasound is focused may be accurately identified using the PCD, and the tumor treatment process may be visualized and identified while ultrasound is being irradiated.

The controller 130 may be implemented with a memory 131 that stores data on an algorithm for controlling the operation of components within the device or a program that reproduces the algorithm, and at least one processor 132 that performs the aforementioned operation using the data stored in the memory 131. Here, the memory 131 and the processor 132 may be implemented as separate chips, respectively. In addition, the memory 131 and the processor 132 may be implemented as a single chip.

The memory 131 may store data supporting various functions of the device, programs for the operation of the controller, may store input/output data, a plurality of application programs (or applications) executed on the device, data for the operation of the device, and commands. At least some of these application programs may be downloaded from an external server via wireless communication.

The memory 131 may include at least one type of storage medium among a flash memory type, a hard disk type, an SSD type (Solid State Disk type), an SDD type (Silicon Disk Drive type), a multimedia card micro type, a card type memory (for example, an SD or XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. In addition, the memory 131 may be a database that is separate from the device but connected by wire or wirelessly.

The processor 132 may control the ultrasonic irradiator 110 to apply preset ultrasonic energy to a focus point of each irradiation area of the human body S based on the cavitation information, or to not apply ultrasonic energy.

Here, the processor 132 may determine whether a tumor is being treated based on the cavitation information. In the case that cavitation information acquired according to the irradiation of ultrasonic energy does not meet a preset condition, the processor 132 may control the ultrasonic irradiator 110 to adjust the ultrasonic energy or to stop the irradiation. In addition, in the case that cavitation information is obtained which indicates cavitation in an area other than the area set to be irradiated with ultrasonic energy, the processor 132 may control the ultrasonic irradiator 110 to adjust the ultrasonic energy or to stop the irradiation.

The processor 132 may determine the acquisition position of the acquisition module 120 for acquiring the cavitation information according to the transmission signal position of the ultrasonic irradiator 110. In the case that the transmission path of the ultrasonic irradiator 110 is changed, the processor 132 may control the acquisition position of the acquisition module 120 to acquire the cavitation information based on a cavitation channel corresponding to the changed transmission path.

The processor 132 may control the ultrasonic irradiator 110 to apply ultrasonic energy with a preset time delay for each transmission signal position of the ultrasonic irradiator 110. In addition, the processor 132 may control the ultrasonic irradiator 110 to apply ultrasonic energy at a preset irradiation time and/or an intensity linked to the transmission signal position of the ultrasonic irradiator 110 and the focus point of each irradiation part of the human body S.

Figure 4:
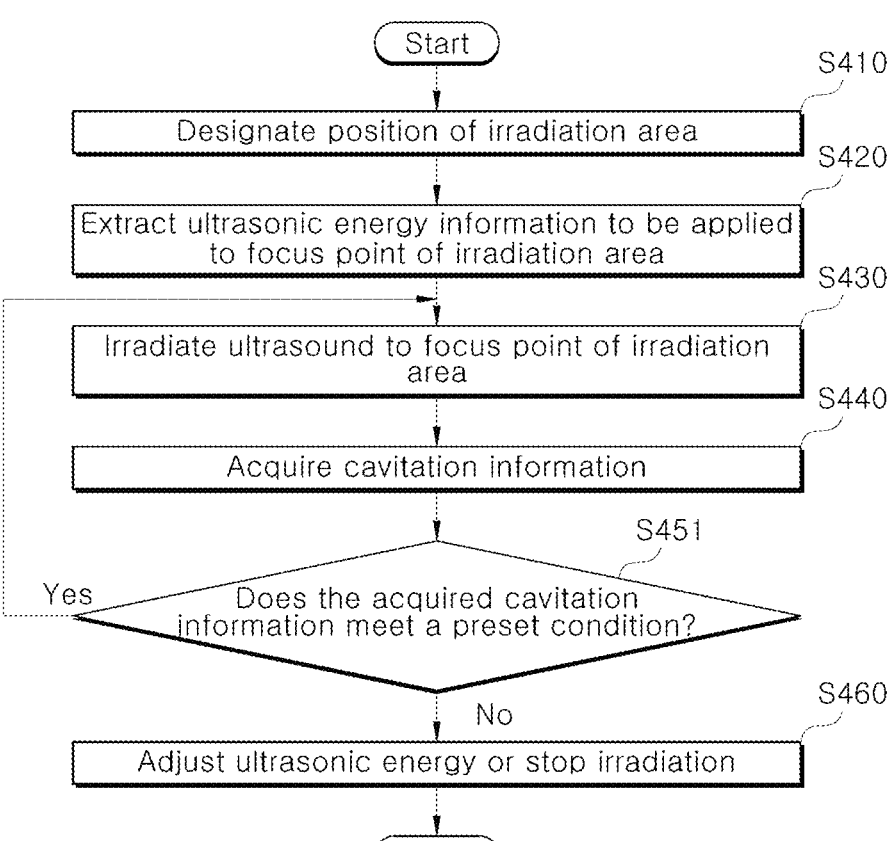
FIG. 4 is a flowchart illustrating an example of an ultrasonic irradiation method according to the present disclosure.
Figures 5, 6:
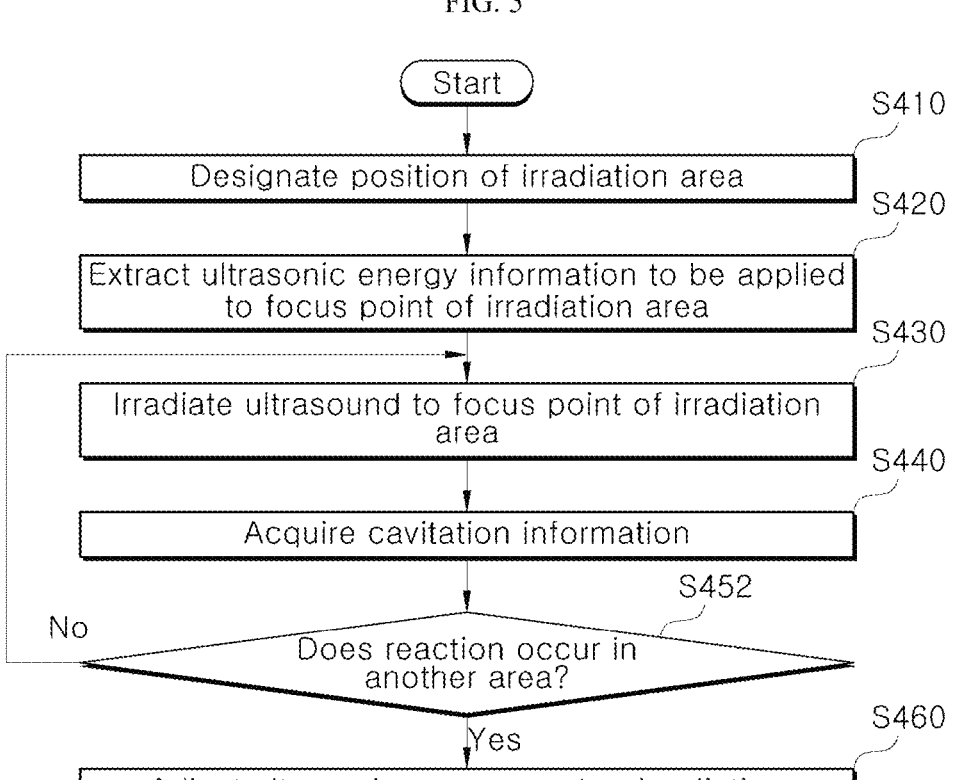
FIG. 5 is a flowchart illustrating another example of an ultrasonic irradiation method according to the present disclosure.
FIGS. 6 to 8 are diagrams illustrating an example of a process for operating a transducer array of an ultrasonic irradiation device.

FIG. 4 is a flowchart illustrating an example of an ultrasonic irradiation method according to the present disclosure. FIG. 5 is a flowchart illustrating another example of an ultrasonic irradiation method according to the present disclosure.

Figure 7:
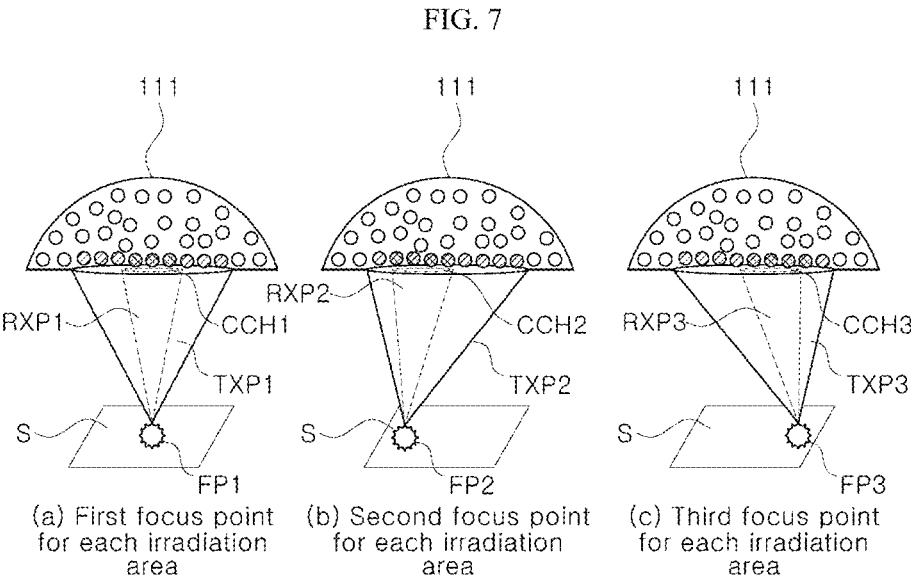
Figure 8:
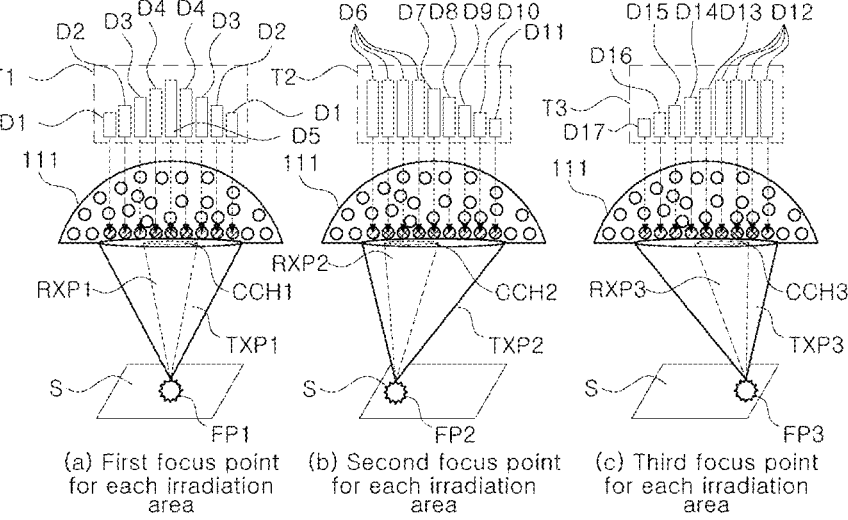

FIGS. 6 to 8 are diagrams illustrating an example of a process in which a transducer array of an ultrasonic irradiator irradiates ultrasound.

Referring to FIGS. 4 to 8, an ultrasonic irradiation method may include a positioning step S410, an extraction step S420, an irradiation step S430, an acquisition step S440, determination steps S451 and S452, and an energy control or irradiation stop step S460.

In the case that the position of the irradiation area of the human body S is designated (step S410) through the ultrasonic irradiator 110, the processor 132 may extract ultrasonic energy information to be applied to the focus point of the irradiation area of the human body S from among the ultrasonic energy information to be applied to the focus point of each preset irradiation area (step S420).

Here, the irradiation area may be at least one of the tumor in an organ S1 of the respiratory organs, an organ S2 of the digestive organs, an organ S3 of the reproductive organs, or an organ S4 of the urinary organs. The ultrasonic energy information may be at least one of the irradiation time or the intensity.

For example, the processor 132 may extract the ultrasonic energy information to be applied to a first focus point FP1 for each irradiation area of the human body S from among the preset ultrasonic energy information. The ultrasonic energy information may be at least one of the first irradiation time or the first intensity to be applied to the first focus point FP1 corresponding to at least one of the tumor in the respiratory organs S1, the digestive organs S2, the reproductive organs S3, or the urinary organs S4.

For another example, the processor 132 may extract the ultrasonic energy information to be applied to a second focus point FP2 for each irradiation area of the human body S from among the preset ultrasonic energy information. The ultrasonic energy information may be at least one of the second irradiation time or the second intensity to be applied to the second focus point FP2 corresponding to at least one of the tumor in the respiratory organs S1, the digestive organs S2, the reproductive organs S3, or the urinary organs S4.

As still another example, the processor 132 may extract the ultrasonic energy information to be applied to a third focus point FP3 for each irradiation area of the human body S from among the preset ultrasonic energy information. The ultrasonic energy information may be at least one of the third irradiation time or the third intensity to be applied to the third focus point FP3 corresponding to at least one of the tumor in the respiratory organs S1, the digestive organs S2, the reproductive organs S3, or the urinary organs S4.

The first irradiation time, the second irradiation time, and the third irradiation time may be different from each other, and the first intensity, the second intensity, and the third intensity may be different from each other.

The processor 132 may control the ultrasonic irradiator 110 to apply ultrasonic energy at least one of the preset irradiation time or the intensity linked to the transmission signal position of the ultrasonic irradiator 110 and the focus point of the irradiation portion of the human body S (step S430).

For example, the processor 132 may control the ultrasonic irradiator 110 to apply ultrasonic energy at a preset first irradiation time and/or a first intensity linked to the first focus point FP1 corresponding to at least one of the tumor in the respiratory organs S1, the digestive organs S2, the reproductive organs S3, or the urinary organs S4.

For another example, the processor 132 may control the ultrasonic irradiator 110 so that the transducer array 111 applies ultrasonic energy at least one of a preset second irradiation time or a preset second intensity to the second focus point FP2 corresponding to at least one of a tumor in an organ S1 of the respiratory organs, an organ S2 of the digestive organs, an organ S3 of the reproductive organs, or an organ S4 of the urinary organs.

For still another example, the processor 132 may control the ultrasonic irradiator 110 so that the transducer array 111 applies ultrasonic energy at a preset third irradiation time and/or a preset third intensity to the third focus point FP3 corresponding to at least one of the tumor in an organ S1 of the respiratory organs, an organ S2 of the digestive organs, an organ S3 of the reproductive organs, or an organ S4 of the urinary organs.

The processor 132 may acquire, through the acquisition module 120, the cavitation information from within the human body S while ultrasound is being irradiated (step S440). Here, the processor 132 may determine whether a tumor is being treated based on the cavitation information.

The acquisition module 120 may include the passive cavitation detector (PCD) to acquire the cavitation information while monitoring the cavitation. For example, the processor 132 may acquire, through the acquisition module 120, the cavitation information for cavitation occurring in at least one of a tumor within an organ S1 of the respiratory organs, an organ S2 of the digestive organs, an organ S3 of the reproductive organs, or an organ S4 of the urinary organs.

That is, as illustrated in FIG. 6, the transducer array 111 may form electron beam steering paths BSP1, BSP2, and BSP3 according to the focus points FP1, FP2, and FP3.

For example, the transducer array 111 may form the first electron beam steering pass BSP1 according to the first focus point FP1. For another example, the transducer array 111 may form the second electron beam steering pass BSP2 according to the second focus point FP2. For another example, the transducer array 111 may form the third electron beam steering pass BSP3 according to the third focus point FP3.

Thereafter, the processor 132 may determine at least one of an acquisition position or an acquisition angle of the acquisition module 120 for acquiring the cavitation information according to a transmission signal position of the transducer array 111. In this process of acquiring the cavitation information, when irradiating ultrasound based on the electronic beam steering scheme, the transmission signal of the transducer array 111 is output in a state where the beam position changes in real time, so the transmission path is continuously changed.

Therefore, according to the present disclosure, at least one of the acquisition position or the acquisition angle of the acquisition module 120 for acquiring the cavitation information may be determined according to the transmission signal position of the transducer array 111.

Here, as illustrated in FIG. 7, in the case of changing between transmission paths TXP1, TXP2, and TXP3 of the transducer array 111, the processor 132 may control at least one of the acquisition position or the acquisition angle of the acquisition module 120 to change between acquiring the cavitation information based on cavitation channels CCH1, CCH2, and CCH3 respectively corresponding to transmission paths TXP1, TXP2, and TXP3.

For example, the processor 132 may control at least one of the acquisition position or the acquisition angle of the acquisition module 120 to acquire the cavitation information through the first cavitation channel CCH1 and a first receiving pass RXP1 that are linked to the first transmitting pass TXP1. The acquisition module 120 may acquire the cavitation information corresponding to the first focus point FP1 for each irradiated area of the human body S.

For another example, the processor 132 may control at least one of the acquisition position or the acquisition angle of the acquisition module 120 to acquire the cavitation information through the second cavitation channel CCH2 and a second receiving pass RXP2 that are linked to the second transmitting pass TXP2. The acquisition module 120 may acquire the cavitation information corresponding to the second focus point FP2 for each irradiated area of the human body S.

For still another example, the processor 132 may control at least one of the acquisition position or the acquisition angle of the acquisition module 120 to acquire the cavitation information through the third cavitation channel CCH3 and a third receiving path RXP3 that are linked to the third transmitting path TXP3. The acquisition module 120 may acquire the cavitation information corresponding to the third focus point FP3 for each irradiated part of the human body S.

As illustrated in FIG. 4, the processor 132 may determine whether cavitation information acquired according to the irradiation of ultrasonic energy meets a preset condition (step S451). In the case that the cavitation information acquired according to the irradiation of ultrasonic energy meets the preset condition, the processor 132 may control the ultrasonic irradiator 110 to irradiate ultrasonic waves, and to apply preset ultrasonic energy linked to the focus point for each irradiation area of the human body S (step S430). For example, in the case that preset first cavitation information is acquired according to the irradiation of the first ultrasonic energy, the processor 132 may control the ultrasonic irradiator 110 to apply preset first ultrasonic energy linked to the focus point for each irradiation area of the human body S.

As illustrated in FIG. 5, the processor 132 may determine whether a reaction occurred in an area other than the area set to be irradiated with ultrasonic energy by determining whether cavitation information is acquired which indicates such a reaction occurred (step S452).

In the case that a reaction occurs only in an area set to be irradiated with ultrasound, the processor 132 may control the ultrasonic irradiator 110 to continue ultrasonic irradiation, and to apply ultrasonic energy linked to the focus point for each irradiated area of the human body S (step S430).

For example, in the case that it is identified that cavitation is not occurring in an area other than the irradiated area and that tissue reaction occurs only in the target area, the processor 132 may control the ultrasonic irradiator 110 to apply ultrasonic energy linked to the focus point for each irradiated area of the human body S.

In addition, the processor 132 may control the ultrasonic irradiator 110 to apply ultrasonic energy with a preset time delay to each transmission signal position of the transducer array 111.

For example, as illustrated in FIG. 8, the processor 132 may control the ultrasonic irradiator 110 to set the first focus point FP1 by applying a time delay D1 to D5 that causes the transducer array 111 to reach a central portion of at least one of a tumor in an organ S1 of the respiratory organs, a tumor in an organ S2 of the digestive organs, a tumor in an organ S3 of the reproductive organs, or a tumor in an organ S4 of the urinary organs differently according to the ultrasonic irradiation time T1, and to apply ultrasonic energy with at least one of the preset first irradiation time or the first intensity linked to the first focus point FP1. The time delay D1 to D5 of the T1 form may become shorter as it goes from the center portion position to the first position deviated off the center portion and the second position deviated off the center portion. That is, the time delay D5 close to the first focus point FP1 may be set to be longer than the other time delays D1 to D4. Without being limited thereto, the present disclosure may also apply other forms of time delay.

For another example, the processor 132 may control the ultrasonic irradiator 110 to set the second focus point FP2 by applying a time delay D6 to D11 that causes the transducer array 111 to reach a first position deviated from the center portion of at least one of the tumor in an organ S1 of the respiratory organs, an organ S2 of the digestive organs, an organ S3 of the reproductive organs, or an organ S4 of the urinary organs, and to apply ultrasonic energy at least one of the second irradiation time or the second intensity that is linked to the second focus point FP2. The time delay D6 to D11 in the form of T2 may become shorter as going to the first position deviated from the center portion, the center portion, and the second position deviated from the center portion. Without being limited thereto, the present disclosure may also apply other forms of time delay.

For another example, the processor 132 may control the ultrasonic irradiator 110 to set the third focus point FP3 by applying a time delay D12 to D17 that causes the transducer array 111 to reach a second position deviated from the center portion of at least one of the tumor in an organ S1 of the respiratory organs, an organ S2 of the digestive organs, an organ S3 of the reproductive organs, or an organ S4 of the urinary organs, and to apply ultrasonic energy at least one of a third irradiation time or a third intensity that is linked to the third focus point FP3. The time delay D12 to D17 in the form of T3 may become shorter as going to the second position deviated from the center portion, the center portion, and the first position deviated from the center portion. Without being limited thereto, the present disclosure may also apply other forms of time delay.

In the case that cavitation information obtained by irradiating ultrasonic energy does not meet a preset condition (step S451), the processor 132 may control the ultrasonic irradiator 110 to adjust the ultrasonic energy or stop irradiation (step S460).

In addition, in the case that cavitation is occurring in an area other than an area set to be irradiated with ultrasound (step S452), the processor 132 may control the ultrasonic irradiator 110 to adjust ultrasonic energy or stop irradiation (step S460). For example, the processor 132 may control the ultrasonic irradiator 110 to stop the irradiation of ultrasound in the case that it is determined that cavitation has occurred in an area other than the irradiation area and that a tissue reaction has occurred. In other words, when ultrasound is irradiated to a first focus point FP1 for an irradiation area, the processor 132 may control the ultrasonic irradiator 110 to adjust ultrasonic energy or stop irradiation in the case that information acquired through the acquisition module 120 indicates that cavitation is occurring at a second focus point FP2 or a third focus point FP3 but not at the first focus point FP1.

Since the present disclosure may adjust ultrasonic energy or stop irradiation in the case that cavitation information obtained according to the irradiation of ultrasonic energy does not meet a preset condition or in the case that a reaction occurs in an area other than the area set to be irradiated with ultrasonic energy, stability during ultrasonic irradiation may be secured.

The ultrasonic irradiation device 100 according to the present disclosure may accurately irradiate ultrasound to a specific irradiation area of the human body without damaging normal tissues in the human body, thereby improving the accuracy of ultrasonic irradiation.

In addition, the ultrasonic irradiation device 100 according to the present disclosure may adjust the ultrasound irradiation parameters for irradiating respective areas of a human body with ultrasonic waves based on optimal condition(s) for each respective area of the human body, thereby maximizing the ultrasonic irradiation effect while reducing the irradiation time.

Meanwhile, the present disclosure may also irradiate ultrasonic waves to each irradiation area of the skin.

The present disclosure may control the ultrasonic irradiator 110 so that, when the ultrasonic irradiator 110 irradiates ultrasound to respective irradiation areas of the skin according to respective ultrasonic irradiation objectives, the ultrasonic irradiator 110 may irradiate the respective irradiation area of the skin with at least one of a depth or an intensity corresponding to the respective ultrasonic irradiation objective based on mapping information that maps the ultrasonic irradiation objective to corresponding depth information and position information of the irradiation area of the skin.

For example, a respective ultrasonic irradiation objective may be related to increasing fat, reducing fat, adding elasticity to dermis or improving skin texture, suppressing wrinkle or acne for reducing pain, removing fat from a cheek, lifting a jawline, and lifting or tightening the skin. In addition, the purpose of ultrasonic irradiation may be to irradiate ultrasound to each skin layer for skin improvement, and may be to irradiate ultrasound to each irradiation area of the human body for improvement of human tissue.

For another example, a respective ultrasonic irradiation objective may correspond to a respective ultrasonic irradiation depth for respective skin layers, and may be to irradiate ultrasound to at least one area among the forehead, the lower jaw, the nasolabial folds, the area around the eyes, the nose, or the upper arm with a specific temperature and specific energy and to at least one ultrasonic irradiation depth among the nipple layer, the upper dermis, the lower dermis, the upper fat layer, the fat layer, the superficial musculoaponeurotic system (SMAS), and the fascia. In addition, the target irradiation objective may include varying the ultrasonic irradiation depth for respective skin layers for skin improvement or varying the ultrasonic irradiation depth for respective irradiation area of the human body for improvement of the human tissue.

The present disclosure may control the ultrasonic irradiator 110 so that the ultrasound is irradiated differently by at least one of the focus depth, irradiation location, intensity, or irradiation time set for each skin layer or irradiation area of the human body according to respective ultrasonic irradiation objectives.

Here, the focus depth may be at least one of deep depth, intermediate depth, or shallow depth set for each skin layer or irradiation area of the human body according to a respective ultrasonic irradiation objective. In addition, the irradiation position may be the entire position or a part of the position set for each skin layer or irradiation area of the human body according to a respective ultrasonic irradiation objective. In addition, the intensity may be at least one of a strong intensity, a medium intensity, or a weak intensity preset for each skin layer or irradiation area of the human body according to a respective ultrasonic irradiation objective. In addition, the irradiation time may be at least one of a fast irradiation time, an average irradiation time, or a slow irradiation time preset for each skin layer or irradiation area of the human body according to a respective ultrasonic irradiation condition. The present disclosure may increase the ultrasonic irradiation effect by controlling the irradiation time at a fast interval and increasing the temperature again before the temperature decreases.

Exemplary embodiments of the present disclosure may be configured so that at least one of the ultrasonic focusing depth, the ultrasonic irradiation position, the ultrasonic intensity, or the ultrasonic irradiation time is finely adjusted within a relevant area since a respective interval between skin layers may be formed differently for each person within the relevant area.

In addition, the present disclosure may control at least one of the angle or the direction of the ultrasonic irradiator 110 so that ultrasound is accurately irradiated to a respective skin layer or a respective irradiation area of the human body at a depth and/or intensity corresponding to a respective ultrasonic irradiation objective, based on at least one of angle information or irradiation direction information.

The present disclosure provides an ultrasonic irradiation device and an irradiation method thereof, which can accurately irradiate ultrasound to a specific part of a body without damaging normal tissues in the body, thereby improving the accuracy of ultrasonic irradiation.

The present disclosure provides an ultrasonic irradiation device and an irradiation method thereof, which can control and irradiate ultrasound to respective parts of a body using optimal condition(s) for each respective part of the body, thereby reducing an irradiation time while maximizing the ultrasonic irradiation effect.

At least one component may be added or deleted in accordance with the performance of the components illustrated in FIG. 1, FIG. 2, FIG. 3, and FIGS. 6 to 8. In addition, it will be appreciated that the reciprocal positions of the components may be changed in accordance with the performance or structure of the system.

Although FIG. 4 and FIG. 5 describe sequential execution of the multiple steps, these are merely exemplary embodiments, and it will be appreciated that the order described in FIG. 4 and FIG. 5 may be modified, and/or with certain operations being performed in parallel, without departing from the principles of the present disclosure.

The disclosed embodiments may be implemented in the form of a non-transitory recording medium that stores instructions executable by a computer. The instructions may be stored in the form of program codes, and when executed by a processor, may generate a program module to perform the operations of the disclosed embodiments. The recording medium may be implemented as a computer-readable recording medium.

The computer-readable recording medium may include any type of recording media that store instructions that can be decoded by a computer. For example, there may be a ROM (Read Only Memory), a RAM (Random Access Memory), a magnetic tape, a magnetic disk, a flash memory, an optical data storage device, and the like.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. An ultrasonic irradiation device, comprising:

an ultrasonic irradiator configured to irradiate ultrasound towards a body of a patient;

a detector configured to acquire cavitation information from a target tumor location of the body of the patient; and a processor configured to:

control the ultrasonic irradiator to irradiate ultrasound towards the body of the patient to treat a tumor at the target tumor location;

determine whether another location other than the target tumor location is being irradiated with ultrasound based on the cavitation information from the detector; and in response to determining that another location other than the target tumor location is being irradiated with ultrasound, control the ultrasonic irradiator to stop irradiating ultrasound.

2. The device of claim 1, wherein the ultrasonic irradiator is configured to irradiate ultrasound based on an electronic beam steering scheme.

3. The device of claim 1, wherein the detector includes a passive cavitation detector (PCD) for acquiring the cavitation information.

4. The device of claim 1, wherein the processor is further configured to:

determine at least one of an acquisition position or an acquisition angle of the detector for acquiring the cavitation information according to a transmission signal position of the ultrasonic irradiator.

5. The device of claim 1, wherein the processor is further configured to:

based on a transmission path of the ultrasonic irradiator being changed, control at least one of an acquisition position or an acquisition angle of the detector to acquire the cavitation information based on a cavitation channel corresponding to the changed transmission path.

6. The device of claim 1, wherein the processor is further configured to:

control the ultrasonic irradiator to irradiate ultrasound with a preset time delay at each transmission signal position of a plurality of transmission signal positions of the ultrasonic irradiator.

7. The device of claim 1, wherein the processor is further configured to:

control the ultrasonic irradiator to irradiate ultrasound using at least one of a preset irradiation time or a preset irradiation intensity corresponding to a transmission signal position of the ultrasonic irradiator and the focus point for a respective irradiation area.

8. An ultrasonic irradiation method, comprising:

irradiating, by an ultrasonic irradiator of an ultrasonic irradiation device, ultrasound towards a body of a patient to treat a tumor at a target tumor location of the body of the patient;

acquiring, by a detector of the ultrasonic irradiation device, cavitation information from the target tumor location of the body of the patient;

determining, by a processor of the ultrasonic irradiation device, whether another location other than the target tumor location is being irradiated with ultrasound based on the cavitation information from the detector; and in response to determining that another location other than the target tumor location is being irradiated with ultrasound, controlling, by the processor of the ultrasonic irradiation device, the ultrasonic irradiator to stop irradiating.

9. The method of claim 8, wherein the ultrasonic irradiator irradiates ultrasound based on an electronic beam steering scheme.

10. The method of claim 8, wherein the detector includes a passive cavitation detector (PCD) for acquiring the cavitation information.

11. The method of claim 8, further comprising:

determining, by the processor, at least one of an acquisition position or an acquisition angle of the detector for acquiring the cavitation information according to a transmission signal position of the ultrasonic irradiator.

12. The method of claim 8, further comprising:

based on a transmission path of the ultrasonic irradiator being changed, controlling, by the processor, at least one of an acquisition position or an acquisition angle of the detector to acquire the cavitation information based on a cavitation channel corresponding to the changed transmission path.

13. The method of claim 8, further comprising:

controlling, by the processor, the ultrasonic irradiator to irradiate ultrasound with a preset time delay at each transmission signal position of a plurality of transmission signal positions of the ultrasonic irradiator.

14. A non-transitory computer-readable medium having processor-executable instructions stored thereon, wherein the processor-executable instructions, when executed, facilitate performance of the following:

irradiating, by an ultrasonic irradiator of an ultrasonic irradiation device, ultrasound towards a body of a patient to treat a tumor at a target tumor location of the body of the patient;

acquiring, by a detector of the ultrasonic irradiation device, cavitation information from the target tumor location of the body of the patient;

determining, by a processor of the ultrasonic irradiation device, whether another location other than the target tumor location is being irradiated with ultrasound based on the cavitation information from the detector; and in response to determining that another location other than the target tumor location is being irradiated with ultrasound, controlling, by the processor of the ultrasonic irradiation device, the ultrasonic irradiator to stop irradiating.

15. The non-transitory computer-readable medium of claim 14, wherein the ultrasonic irradiator irradiates ultrasound based on an electronic beam steering scheme.

16. The non-transitory computer-readable medium of claim 14, wherein the detector includes a passive cavitation detector (PCD) for acquiring the cavitation information.

17. The non-transitory computer-readable medium of claim 14, wherein the processor-executable instructions, when executed, further facilitate performance of the following:

determining, by the processor, at least one of an acquisition position or an acquisition angle of the detector for acquiring the cavitation information according to a transmission signal position of the ultrasonic irradiator.

18. The non-transitory computer-readable medium of claim 14, wherein the processor-executable instructions, when executed, further facilitate performance of the following:

based on a transmission path of the ultrasonic irradiator being changed, controlling, by the processor, at least one of an acquisition position or an acquisition angle of the detector to acquire the cavitation information based on a cavitation channel corresponding to the changed transmission path.

19. The non-transitory computer-readable medium of claim 14, wherein the processor-executable instructions, when executed, further facilitate performance of the following:

controlling, by the processor, the ultrasonic irradiator to irradiate ultrasound with a preset time delay at each transmission signal position of a plurality of transmission signal positions of the ultrasonic irradiator.

20. The non-transitory computer-readable medium of claim 14, wherein the processor-executable instructions, when executed, further facilitate performance of the following:

controlling, by the processor, the ultrasonic irradiator to irradiate ultrasound using at least one of a preset irradiation time or a preset irradiation intensity corresponding to a transmission signal position of the ultrasonic irradiator and the focus point for a respective irradiation area.

\* \* \* \* \*